(12) United States Patent
Sugimoto

(10) Patent No.: US 7,871,370 B2
(45) Date of Patent: Jan. 18, 2011

(54) ENDOSCOPE-SHAPE MONITORING SYSTEM

(75) Inventor: Hideo Sugimoto, Tokyo (JP)

(73) Assignee: Hoya Corporation, Tokyo (JP)

( * ) Notice: Subject to any disclaimer, the term of this patent is extended or adjusted under 35 U.S.C. 154(b) by 978 days.

(21) Appl. No.: 11/557,517

(22) Filed: Nov. 8, 2006

(65) Prior Publication Data
US 2007/0106115 A1 May 10, 2007

(30) Foreign Application Priority Data
Nov. 9, 2005 (JP) .......................... P2005-325225

(51) Int. Cl.
A61B 1/00 (2006.01)
(52) U.S. Cl. .................. 600/117; 600/145; 600/424
(58) Field of Classification Search .............. 600/117, 600/118, 138, 139, 141, 145, 146, 424
See application file for complete search history.

(56) References Cited

U.S. PATENT DOCUMENTS

| 5,253,647 | A | | 10/1993 | Takahashi et al. | |
|---|---|---|---|---|---|
| 5,728,044 | A | * | 3/1998 | Shan | 600/145 |
| 5,840,024 | A | | 11/1998 | Taniguchi et al. | |
| 5,997,473 | A | | 12/1999 | Taniguchi et al. | |
| 6,059,718 | A | * | 5/2000 | Taniguchi et al. | 600/117 |
| 6,203,493 | B1 | * | 3/2001 | Ben-Haim | 600/117 |
| 6,432,041 | B1 | | 8/2002 | Taniguchi et al. | |
| 6,689,049 | B1 | * | 2/2004 | Miyagi et al. | 600/117 |
| 6,773,393 | B1 | | 8/2004 | Taniguchi et al. | |
| 2004/0176683 | A1 | * | 9/2004 | Whitin et al. | 600/424 |
| 2006/0009679 | A1 | * | 1/2006 | Ito et al. | 600/117 |

FOREIGN PATENT DOCUMENTS

| JP | 11-225942 | 8/1999 |
|---|---|---|
| JP | 3362906 | 10/2002 |
| JP | 2003-52611 | 2/2003 |
| JP | 3458060 | 8/2003 |

OTHER PUBLICATIONS

U.S. Appl. No. 11/557,510 to Sugimoto, filed Nov. 8, 2006.
U.S. Appl. No. 11/557,536 to Sugimoto, filed Nov. 8, 2006.
English language Abstract of JP 11-225942.
English language Abstract of JP 2003-52611.

* cited by examiner

Primary Examiner—John P Leubecker
Assistant Examiner—Jeffrey H Chang
(74) Attorney, Agent, or Firm—Greenblum & Bernstein P.L.C.

(57) ABSTRACT

An endoscope shape monitoring system that is used to grasp a shape of a flexible insertion portion is provided that includes a position detector and a determining processor. The position detector detects a plurality of positions of the insertion portion along the central axis of the insertion portion at predetermined intervals. The determining processor determines the position of at least one of the central axis or an outline of the insertion portion.

5 Claims, 6 Drawing Sheets

ENDOSCOPE-SHAPE MONITORING SYSTEM

BACKGROUND OF THE INVENTION

1. Field of the Invention

The present invention relates to a system or to an apparatus that is used for monitoring the shape of an insertion portion or a flexible tube of an endoscope that is inserted inside a cavity or a hollow of an object.

2. Description of the Related Art

It is beneficial for an endoscopic operator to grasp the shape of a flexible tube of an endoscope that is inserted inside a body. In particular, the visualization of the endoscope shape inside the body has a significant advantage when operating a lower intestinal endoscope, such as a colonoscope, since insertion of the flexible tube into a tortuous intestine is difficult. As a result, various types of endoscope-shape monitoring systems have been proposed.

A system that uses an alternating magnetic field for detecting a shape of a flexible tube of an endoscope is conventionally known. In this system, a plurality of coils are disposed along the longitudinal direction of the flexible tube, and a three-dimensional position and a direction for each of the coils are detected by using electromagnetic interactions between the alternating magnetic field and the coils. For example, the shape of the flexible tube is represented by a three-dimensional spline curve, which is obtained from position data of measurement points where the coils are placed, and the result is displayed on a monitor.

However, it is not easy for a user to grasp the shape of the flexible tube when the shape is merely represented by a simple curve or a simple line graph, since the flexible tube has an actual thickness. Thus, in U.S. Pat. No. 5,253,647, the shape of a flexible tube is described as a tube with a thickness so as to suit the actual shape of the flexible tube.

SUMMARY OF THE INVENTION

However, the position of the tube displayed on the monitor is generally not in a proper position, since the magnetic sensors or the coils are normally not arranged along the central axis of the flexible tube. This problem becomes prominent if the magnetic sensors are only used to detect the positions thereof, or if the angular measurements are not available.

Therefore, an object of the present invention is to provide an endoscope-shape monitoring system or apparatus that enables a user visually and accurately to grasp the shape, position, and size of a flexible tube of an endoscope inserted inside an object.

According to the present invention, an endoscope-shape monitoring system that is used to grasp the shape of a flexible insertion portion is provided. The system includes a position detector and a determining processor. The position detector detects a plurality of positions of an insertion portion along the central axis of the insertion portion at predetermined intervals. The determining processor determines the position of at least one of the central axis or an outline of the insertion portion.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
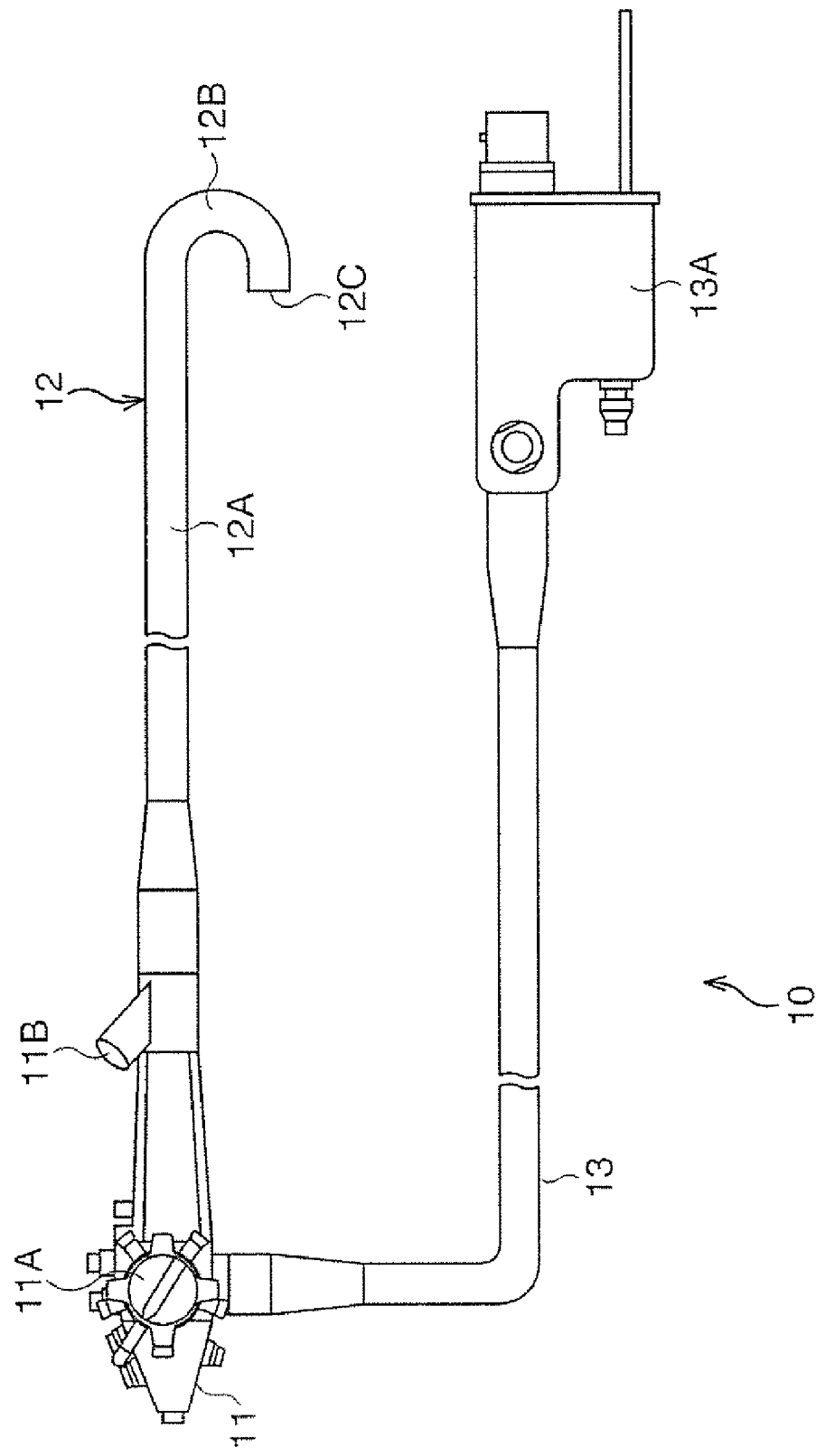
FIG. 1 is a general view of an endoscope to which an endoscope shape monitoring system as an embodiment of the present invention is applied.

The present invention is described below with reference to the embodiments shown in the drawings.

FIG. 1 is a general view of an endoscope to which an embodiment of an endoscope-shape monitoring system of the present invention is applied. In this embodiment, an electronic endoscope is employed as an example for the endoscope.

The electronic endoscope 10 has an operating portion 111, which an endoscopic operator manipulates. An insertion portion (a flexible tube) 12 and a light-guide cable 13 are both connected to the operating portion 111. A connector 13A is provided at the distal end of the light-guide cable 13. The connector 13A is detachably attached to a processor unit (not depicted), for example, in which a light source and an image-signal processing unit are integrally installed. Namely, illumination light from the light source inside the processor unit is supplied to a cavity or a hollow viscus through the connector 13A of the electronic endoscope 10 and the light-guide cable 13. Further, image signals from the electronic endoscope 10 are supplied to the image-signal processing unit inside the processor unit.

The insertion portion 12 is comprised of a flexible portion 12A, a bendable portion 12B, and a distal end portion 12C. Most part of the insertion portion 12 is occupied by the flexible portion 12A that is formed of a flexible tube, which is freely bendable, and the flexible portion 12A is directly connected to the operating portion 111. The bendable portion 12B is provided between the distal end portion 12C and the flexible portion 12A, and bent in accordance with a rotational operation of an angle lever 11A that is provided on the operating portion 111. For example, the bendable portion 12B can be bent as far as the direction of the distal end portion 12C being rotated 180 degrees. Further, as it will be detailed later, the distal end portion 12C is provided with an imaging optical system, an imaging device, an illuminating optical system, and other components.

Figure 2:
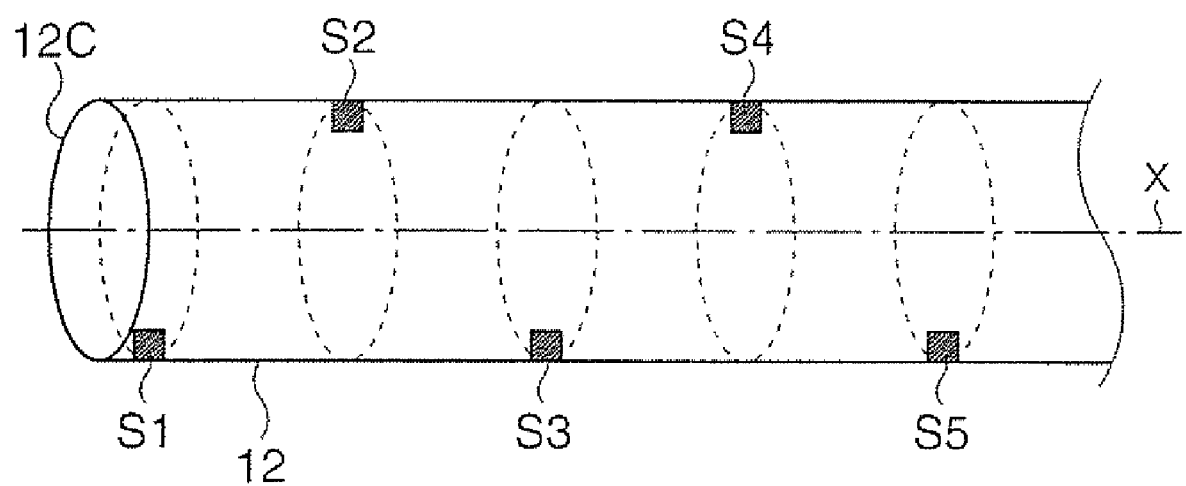
FIG. 2 schematically illustrates an arrangement of coils provided inside an insertion portion.
Figure 3:
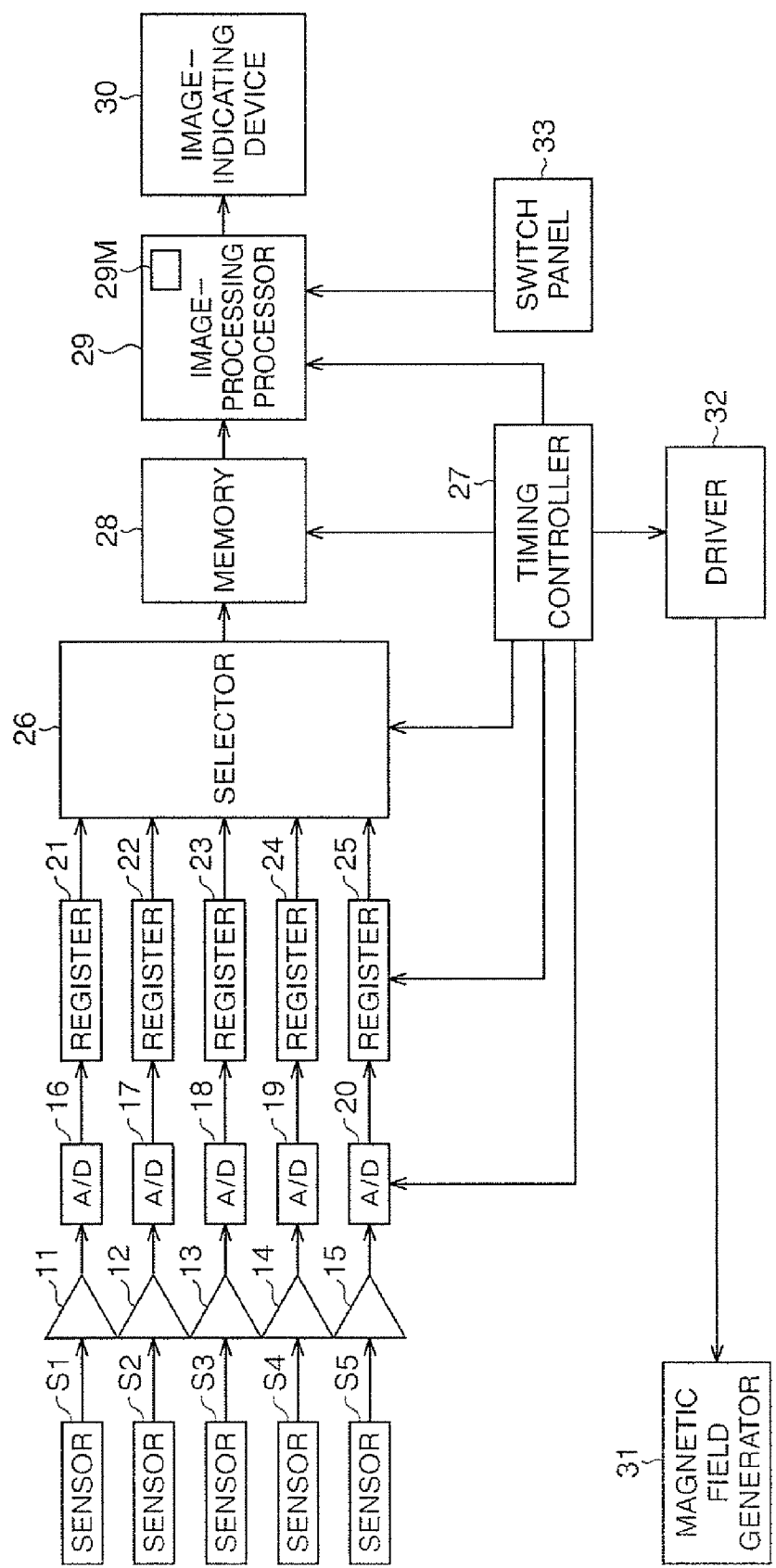
FIG. 3 is a block diagram that shows electrical structures of the endoscope shape monitoring system.

FIG. 2 schematically illustrates an arrangement of magnetic sensor coils installed inside the insertion portion 12. FIG. 3 is a block diagram of an endoscope-shape monitoring system of the present embodiment that detects positions of the insertion portion 12 and displays the shape of the insertion portion 12. In FIGS. 2 and 3, five magnetic sensor coils are shown as an example.

As illustrated in FIG. 2, the coils (magnetic sensors) S1-S5 are arranged along the central axis of the insertion portion 12 at predetermined intervals. Further, the coils S1-S5 are alternately arranged with respect to the central axis. Namely, in the present embodiment, the coils S1-S5 are so arranged that the position of the central axis or the outline of the insertion portion 12 can be determined from the detected positions of the coils S1-S5.

As for the endoscope-shape monitoring system shown in FIG. 3, elements other than the coils (magnetic sensors) S1-S5 and a magnetic field generator 31 are, for example, provided in the operating portion 111 or inside the processor unit (not shown). The coils S1-S5 are connected, respectively, to corresponding amplifiers 11-15, and the amplifiers 11-15 are connected, respectively, to corresponding A/D converters 16-20. Further, the A/D converters 16-20 are connected, respectively, to corresponding registers 21-25, and the registers 21-25 are connected to selector 26.

Therefore, signals detected by each of the coils S1-S5 are amplified by the amplifiers 11-15 by a predetermined gain and are converted, respectively, to digital signals by the A/D converters 16-20. Further, the digital signals are temporary stored in the registers 21-25. One of the signals stored in the registers 21-25 is selected by the selector 26, according to timing control carried out by a timing controller 27, so that the signals for each of the coils S1-S5 are, in turn, fed to a memory 28 at a predetermined timing.

A set of data that is obtained for the coils S1-S5 at a certain point in time is stored in the memory 28 and then fed to an image-processing processor 29. The image-processing processor 29 calculates the positions of the coils S1-S5, and generates image data that describes a shape of the tube for the insertion portion 12 at appropriate arrangement with respect to the coils S1-S5, based on the calculated positions of the coils S1-S5. The image data are then fed to the image-indicating device 30. Thus, a tubular shape of the insertion portion 12 is properly displayed on the image-indicating device 30.

The positional data of each coil may be maintained in a memory 29M that is provided inside the image-processing processor 29 (or in the memory 28), so that a three-dimensional image of the insertion portion 12 is displayed on the image-indicating device 30. Namely, the three-dimensional image of the insertion portion 12 may be rotated by operating switches on a switch panel 33 that is connected to the image-processing processor 29.

Further, the positions of the coils S1-S5 are obtained by detecting the effects of electromagnetic interactions to the coils S1-S5, where the effects are induced by the alternating magnetic field. For example, as is known in the art, the magnetic field generator 31 generates alternating magnetic fields in turn for each of the X, Y, and Z coordinates of an orthogonal coordinate system XYZ. The magnetic field generator 31 is controlled by a driver 32, and the driver 32 is controlled by the timing controller 27.

Figure 4:
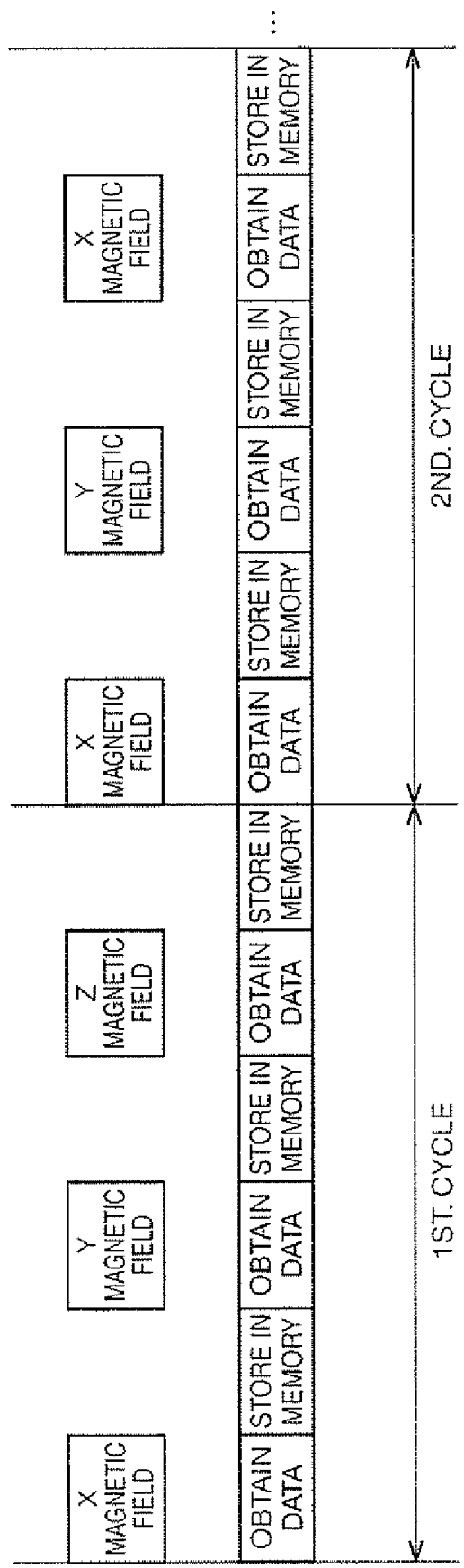
FIG. 4 is a timing chart that shows an example of timing for the magnetic field generator to generate a magnetic field and for the coil (sensor) to obtain signals.

FIG. 4 is a timing chart that shows an example of timing for the magnetic field generator 31 to generate a magnetic field, and of timing for the coil (sensor) to obtain signals. In FIG. 4, only data obtained during two cycles are indicated.

As shown in FIG. 4, primarily, the magnetic field generator 31 generates a magnetic field in the X-axis direction, so that signals are detected by each of the coils SL-S5 and data of the signals from the coils S1-S5, which relate to the X-axis, are temporarily stored in the registers 21-25. The data for the X-axis, which are stored in the registers 21-25, are then stored in the memory 28 via the selector 26.

In turn, the magnetic field generator 31 generates a magnetic field in the Y-axis direction, so that signals are detected by each of the coils S1-S5, and data of the signals from the coils S1-S5, which relate to the Y-axis, are temporarily stored in the registers 21-25. The data for the Y-axis are then stored in the memory 28 via the selector 26. In the same way, a magnetic field in the Z-axis direction is then generated, and the data for the Z-axis are then stored in the memory 28.

As described above, the signal data of the coils S1-S5 for the X-axis, the Y-axis, and the Z-axis are obtained and stored in the memory 28, so that the three-dimensional positions of the coils S1-S5 in the first cycle are determined from the signal data.

The same is true in the second cycle. Namely, the signal data of the coils S1-S5 for the X-axis, the Y-axis, and the Z-axis in the second cycle are obtained and stored in the memory 28, and the three-dimensional positions of the coils S1-S5 in the second cycle are determined from the signal data. Thereby, the positions of the coils S1-S5 are sequentially detected in real time.

Figure 5:
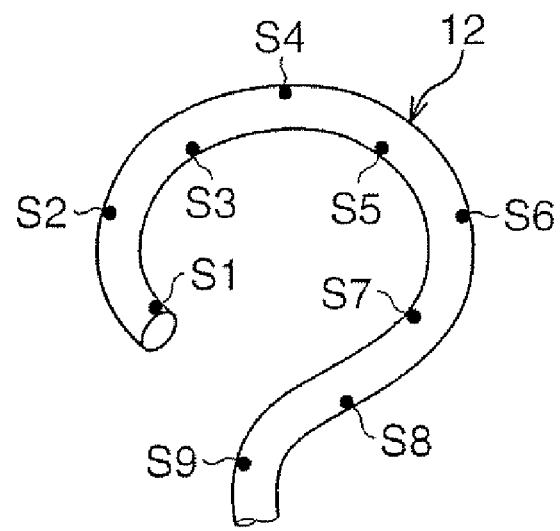
FIG. 5 illustrates an example of a tubular-shaped image of the insertion portion that is produced from the positions of the coils (magnetic sensors)

In FIG. 5, an example of a tubular-shaped image for the insertion portion 12 that is produced from the positions of the coils (magnetic sensors), which are detected at a certain time (in a cycle), is illustrated. In FIG. 5, nine coils (magnetic sensors) S1-S9 are indicated as an example.

In the present embodiment, the coils are alternately disposed on either side of the central axis of the insertion portion 12 from the distal end of the insertion portion 12, so that, for example, an outline of the insertion portion 12 on one side is obtained from the positions of the coils odd-numbered from the distal end portion 12C, and an outline of the other side from the positions of the even-numbered coils. Thereby, the insertion portion 12 is displayed as a tube having a thickness, and the central axis of the flexible tube is indicated at approximately the correct position with respect to each of the coils.

Further, the actual thickness of the insertion portion 12 can be calculated by comparing the position of the coil S2 to the position of the coil S1, and the positions of the coil S2 and the coil S4 to the position of the coil S3. Thus, the represented dimensional ratio of the thickness of the tube as indicated in the image, can be adapted to the actual dimensional ratio of the flexible tube or insertion portion 12.

As described above, according to the present embodiment, the insertion portion of the endoscope is indicated on the monitor as a tubular shape that is adjusted to the actual dimensions of the insertion portion. Therefore, an endoscopic operator can visually and accurately grasp the shape, the position, and the dimensions of the insertion portion that has been inserted inside a patient body.

Note that, in the present embodiment, although a pair of side outlines for the flexible tube or the insertion portion are obtained from the positions of the odd-numbered coils and the even-numbered coils, the tubular shape can also be obtained by using an interpolation line for the central axis of the insertion portion, which is calculated from the positions of the coils and the thickness of the insertion portion.

Figure 6:
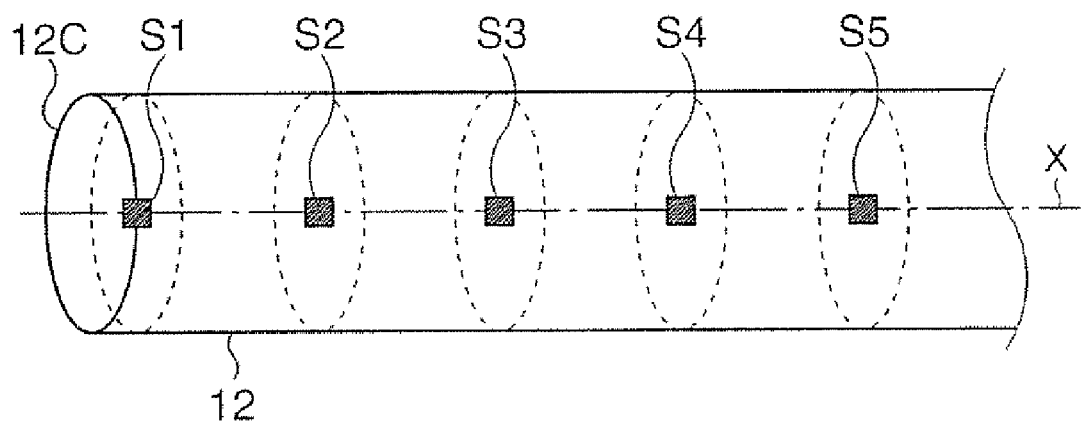
FIG. 6 schematically illustrates an alternative embodiment in which the coils are arranged on and along the central axis.
Figure 7:
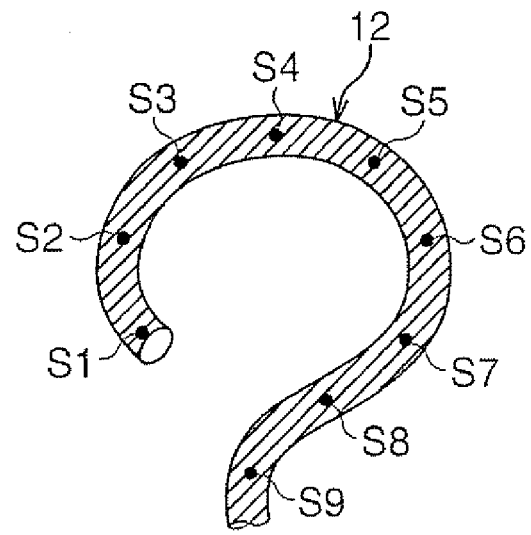
FIG. 7 illustrates an example of a tubular-shaped image for the insertion portion that is produced from the positions of the coils in the alternative embodiment.

Further, in the present embodiment, the coils (magnetic sensors) are alternately arranged. However, the arrangement of the coils is not restricted to that of the embodiment, if the arrangement can determine the central axis of the insertion portion or the outline of the insertion portion. For example, the coils can be disposed on and along the central axis, as shown in FIG. 6. In this case, the tubular shape of the insertion portion indicated on the monitor is displayed as shown in FIG. 7. For example, the diameter of the insertion portion may be stored in a memory provided inside the endoscope, so that the outline may be obtained from the diameter that is adapted to the scale of the coils indicated on the image-indicating device.

Moreover, when the positions of the coils are biased in a certain direction, the position of the central axis or the outline can be acquired by taking the displacement into consideration. Note that a method of undetermined coefficient, a least square method, or the like can be used to acquire the central axis or the outline of the insertion portion.

Figure 8:
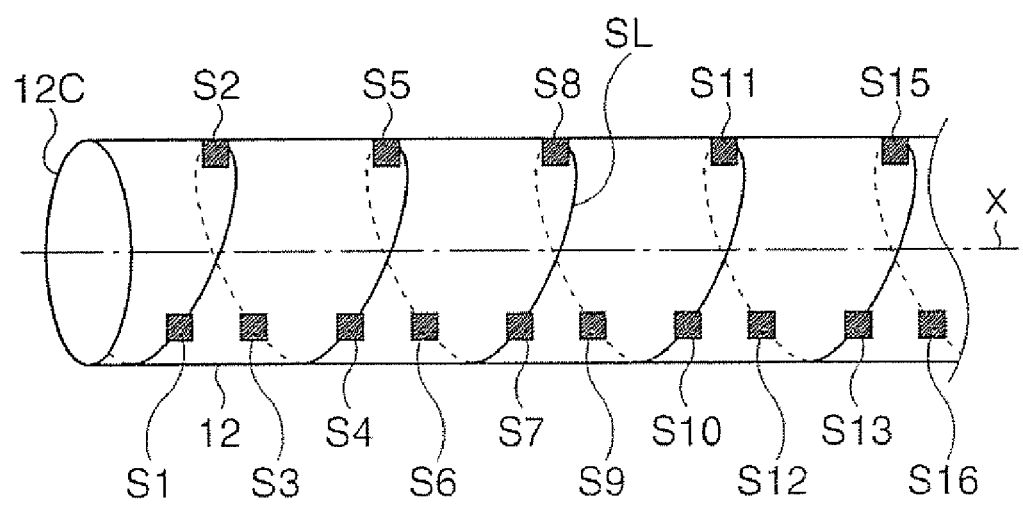
FIG. 8 schematically illustrates an alternative embodiment in which the coils are arranged along a spiral that is coaxial with the central axis of the insertion portion.

Further, as shown in FIG. 8, the coils can also be arranged along a spiral SL that is coaxial with the central axis of the insertion portion.

In the present embodiment, the alternating magnetic field is generated by the magnetic field generator disposed outside an inspection object and the coils, as the magnetic sensors are disposed inside the insertion portion. However, the coils for generating a magnetic field can be disposed inside the insertion portion, and magnetic sensors can be disposed outside the inspection object.

Although the embodiment of the present invention has been described herein with reference to the accompanying drawings, obviously many modifications and changes may be made by those skilled in this art without departing from the scope of the invention.

The present disclosure relates to subject matter contained in Japanese Patent Application No. 2005-325225 (filed on Nov. 9, 2005), which is expressly incorporated herein, by reference, in its entirety.

The invention claimed is:

1. An endoscope shape monitoring system that is used to grasp the shape of a flexible insertion portion, the system comprising:
   a position detector that detects a plurality of positions of said insertion portion on either side of the central axis of said insertion portion at predetermined intervals;
   a thickness calculator that calculates an actual thickness of said insertion portion based on detected positions of an adjacent two of said plurality of positions that are provided on sides of the central axis opposite to each other;
   a determining processor that determines a position of an outline of said insertion portion; and
   an image generator that generates a tubular shape image of said insertion portion based on said calculated thickness and said outline.

2. The system as claimed in claim 1,
   wherein said position detector comprises a plurality of sensors for detecting said plurality of positions, said plurality of sensors being disposed alternately on either side of said central axis, and
   wherein said plurality of positions are detected positions of said plurality of sensors.

3. The system as claimed in claim 2,
   wherein said position detector applies an alternating magnetic field.

4. The system as claimed in claim 3,
   wherein said position detector comprises a magnetic field generator that generates said alternating magnetic field, and said plurality of sensors comprises a plurality of coils for detecting said alternating magnetic field, so that said plurality of positions is obtained from signals from said plurality of coils.

5. The system as claimed in claim 1,
   wherein said position detector comprises a plurality of sensors for detecting said plurality of positions, and said plurality of sensors are arranged along a spiral that is coaxial with the central axis of said insertion portion,
   wherein said plurality of positions are detected positions of said plurality of sensors.

* * * * *